United States Patent
Gharib et al.

(10) Patent No.: US 6,956,230 B1
(45) Date of Patent: *Oct. 18, 2005

(54) INTEGRATED PARTICLES SENSOR FORMED ON SINGLE SUBSTRATE USING FRINGES FORMED BY DIFFRACTIVE ELEMENTS

(75) Inventors: Morteza Gharib, San Marino, CA (US); Dominique Fourguette, Los Angeles, CA (US); Darius Modarress, Los Angeles, CA (US); Frederic Taugwalder, Altadena, CA (US); Siamak Forouhar, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 544 days.

This patent is subject to a terminal disclaimer.

(21) Appl. No.: 09/838,344

(22) Filed: Sep. 15, 2000

Related U.S. Application Data

(60) Provisional application No. 60/154,486, filed on Sep. 17, 1999, and provisional application No. 60/154,487, filed on Sep. 17, 1999.

(51) Int. Cl.[7] .............................................. G01N 21/49
(52) U.S. Cl. ...................... 250/574; 356/336; 356/441; 73/865.5; 73/705
(58) Field of Search ................... 356/35, 49, 335–342, 356/354, 28, 442; 73/865.5, 147, 705; 250/550, 237 G, 222.2, 224, 573, 574

(56) References Cited

U.S. PATENT DOCUMENTS

| | | | |
|---|---|---|---|
| 3,216,318 A | * 11/1965 | Gaffard | ........................ 353/97 |
| 3,548,655 A | * 12/1970 | Rudd | ......................... 356/28.5 |
| 4,373,807 A | 2/1983 | Gouesbet | |
| 4,896,098 A | * 1/1990 | Haritonidis et al. | ......... 324/663 |
| 4,948,257 A | 8/1990 | Kaufman et al. | |
| 5,052,228 A | * 10/1991 | Haritonidis | ................... 73/705 |
| 5,160,976 A | 11/1992 | Carr et al. | |
| 5,199,298 A | * 4/1993 | Ng et al. | .................... 73/54.01 |
| 5,327,218 A | * 7/1994 | Igaki | ........................... 356/499 |
| 5,453,837 A | 9/1995 | Naqwi et al. | |
| 5,680,211 A | * 10/1997 | Kaneda et al. | ............... 356/499 |
| 5,701,172 A | * 12/1997 | Azzazy | ........................ 356/28 |
| 5,835,217 A | * 11/1998 | Medecki | ...................... 356/521 |
| 5,998,782 A | * 12/1999 | Koyama et al. | .......... 250/222.2 |
| 6,249,351 B1 | * 6/2001 | de Groot | ..................... 356/512 |

* cited by examiner

*Primary Examiner*—Jay Patidar
(74) *Attorney, Agent, or Firm*—Fish & Richardson P.C.

(57) ABSTRACT

Integrated sensors are described using lasers on substrates. In one embodiment, a first sensor forms a laser beam and uses a quartz substrate to sense particle motion by interference of the particles with a diffraction beam caused by a laser beam. A second sensor uses gradings to produce an interference. In another embodiment, an integrated sensor includes a laser element, producing a diverging beam, and a single substrate which includes a first diffractive optical element placed to receive the diverging beam and produce a fringe based thereon, a scattering element which scatters said fringe beam based on particles being detected, and a second diffractive element receiving scattered light.

24 Claims, 8 Drawing Sheets

US 6,956,230 B1

INTEGRATED PARTICLES SENSOR FORMED ON SINGLE SUBSTRATE USING FRINGES FORMED BY DIFFRACTIVE ELEMENTS

CROSS-REFERENCE TO RELATED APPLICATIONS

This application claims benefit of U.S. Provisional application No. 60/154,486, and No. 60/154,487, both filed Sep. 17, 1999.

STATEMENT AS TO FEDERALLY-SPONSORED RESEARCH

U.S. Government may have certain rights in this invention pursuant to Darpa grant number N66001-99-1-8902 and U.S. Navy grant no. N00014-99-1-0297.

The invention described herein was made in the performance of work under a NASA contract, and is subject to the provisions of Public Law 96-517 (U.S.C. 202) in which the contractor has elected to retain title.

BACKGROUND

It is often desirable to obtain different kinds of information about particles.

One kind of information is about shear stress. An existing method of detecting wall shear stress puts a heated wire or element in the flow to be detected. The rate of cooling of the element provides a measure of the wall shear stress. Other similar sensors, which sense other parameters, are also known.

However, this system by itself has certain problems. The techniques may be intrusive, meaning that they may effect the rate of flow. The techniques can be affected by contaminants in the flow. For example, certain contaminants may deposit on the heated element and cause the heated element to react differently. These techniques can also change the characteristics of the sensor; hence requiring calibration.

Non-intrusive optical techniques may be considered using conventional optics. However, this results in a bulky setup, and setup that is highly susceptible to vibration. Moreover, the size of such a setup may cause difficulty in allowing the system to be effectively used.

Other kinds of probes can be used to detect the size of particles, and may have similar drawbacks.

SUMMARY

The present application teaches integrated optical sensors for detecting particle details.

One aspect detects and/or measures wall shear stress in flows.

BRIEF DESCRIPTION OF THE DRAWINGS

These and other aspects will now be described in detail with reference to the accompanying drawings wherein.

DETAILED DESCRIPTION

The present application teaches a special miniaturized and integrated optical sensor probe for measuring wall shear stress in aerodynamic and hydrodynamic flows for example. As described herein, the system also provides structure which is highly minaturizable, and which can be formed within a housing of a special type that enables the use of the sensor in harsh environments. Moreover, the system in is non-intrusive and non-invasive. The center of the probe's volume may be located very close to the surface being measured, e.g. as close as 100 microns to the surface. Moreover, the sensor as described herein may be configured in a way, as described herein, that may require less calibration.

Figure 1:
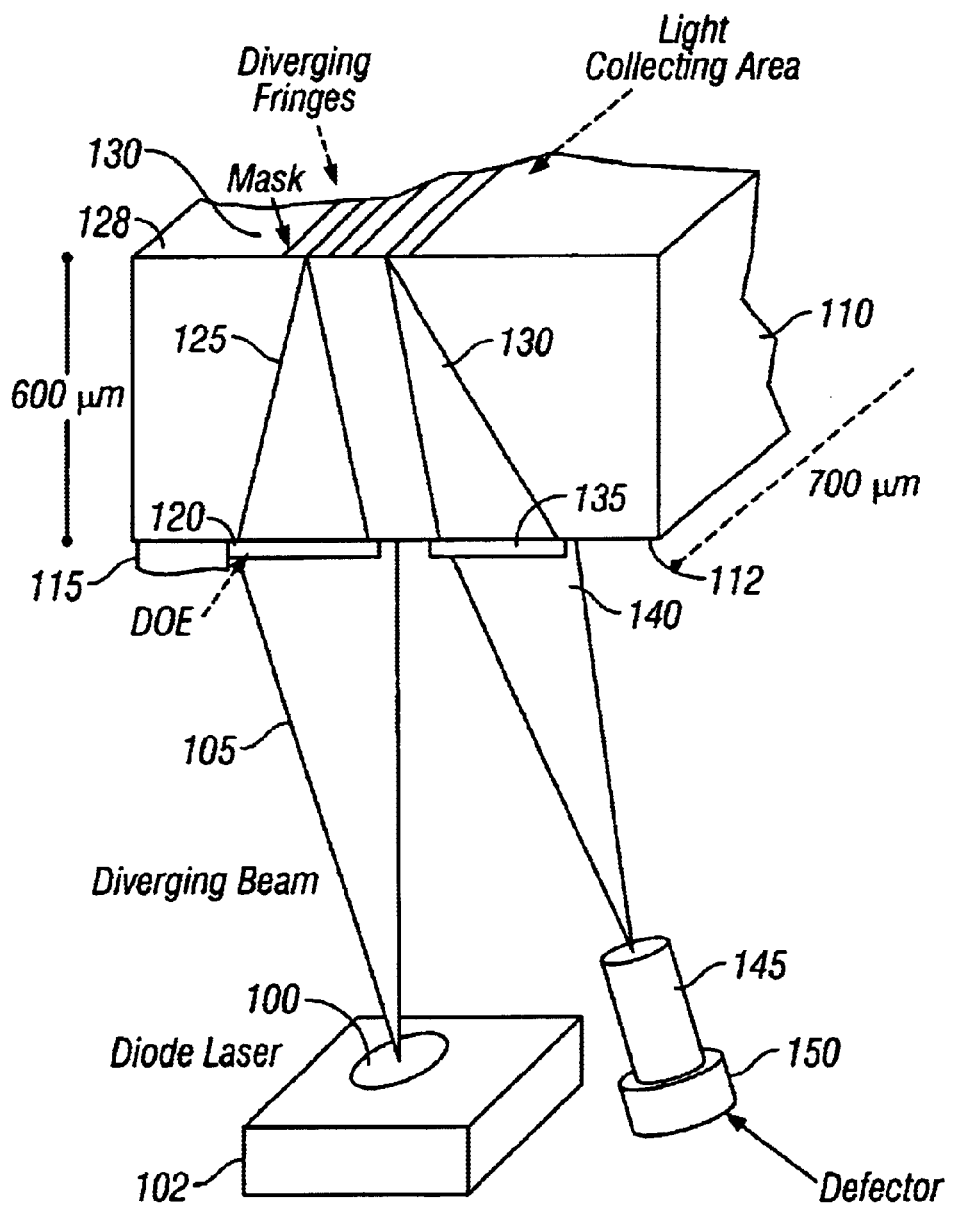
FIG. 1 shows a schematic for a first wall stress sensor.

A schematic of the sensor is shown in FIG. 1. A diode laser 100 is formed on a substrate 102. The diode laser produces a diverging output beam 105 which diverges at a specified angle. The output beam is shaped, for example, into two, parallel very high aspect ratio ellipses. The beam is coupled toward a transparent substrate, e.g., a quartz substrate 110 which forms an optical assembly. The quartz substrate may have a size, for example, of 600 microns thick and 700 microns square on a side. The quartz substrate 110 includes a metal film 115 formed thereon, e.g., a film formed of chromium or aluminum. The metal film is processed to form specified openings therein. Optical slits are formed in an area 120 of the metal film, arranged to form a diffractive optical element. The slits can be fabricated by etching the metal from the thin film in a specified pattern.

Figure 2:
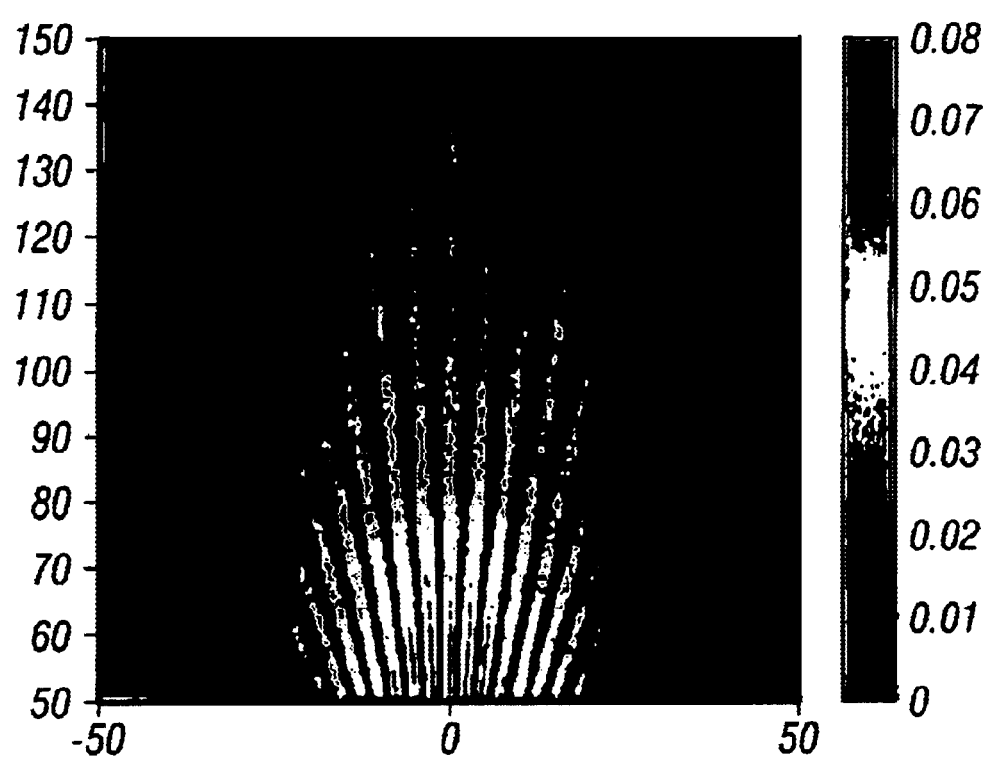
FIG. 2 shows an optical fringe pattern emitted by the sensor of FIG. 1.

The light exiting from the diffractive optical element 120 forms a two-dimensional, linearly diverging optical fringe pattern 125. The optical fringe pattern can, for example, simply include diverging fringes. The fringe pattern may be of the type shown in FIG. 2 where the pattern width is on the order of 25 microns, and the position is on the order of 90 microns for the main part of the fringe, with the edges of the fringe ending at 130–140 microns.

The fringe 125 impinges on a mask 130 which is formed on the second surface 128 of the quartz substrate 110.

The second surface 128 of the quartz substrate is placed near the flow to be measured. Light is scattered off the particles crossing the fringe pattern to form reflected beam 130.

Scattered light is also obtained by a second optical window 135 that is formed in the metal film 115. The light is collected through that optical window, via another diffractive optical element 140 formed on the surface of the quartz element. The scattered light is collected by those elements and focused onto an optical fiber detector 145. An avalanche photodiode 150 can be located at the end of the detector, receiving the light therefrom.

Figure 3:
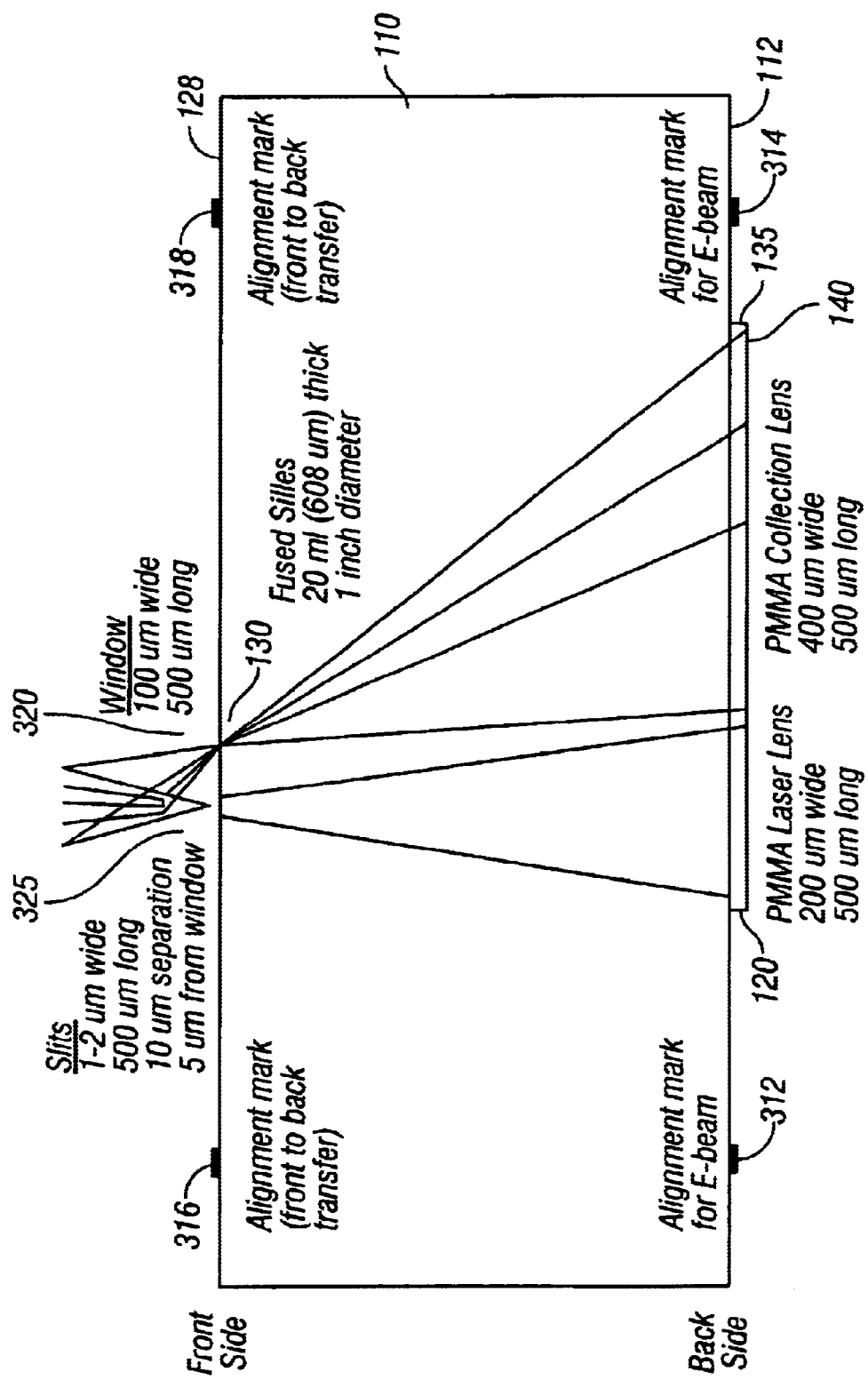
FIG. 3 shows a details of fabrication of the optical part.
Figure 4:
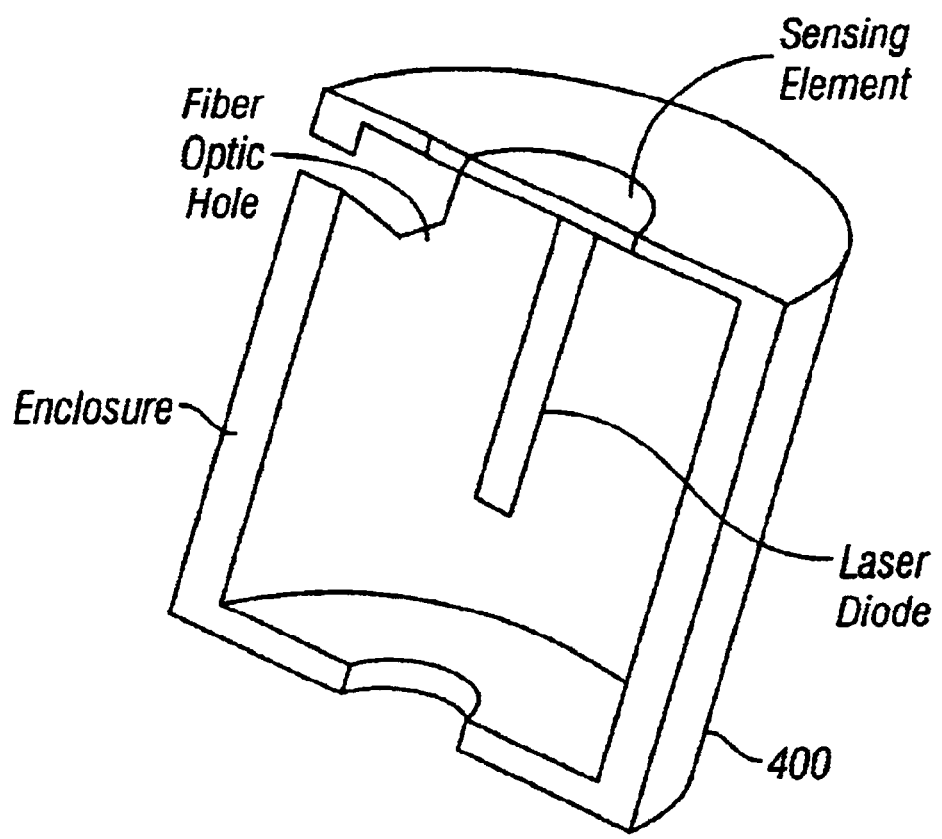
FIG. 4 shows an assembly drawing showing the way in which the elements are held within a housing.

An important feature of system in FIG. 1 is that the sensor element can be fabricated using micro-fabrication technology. The substrate 110 can be formed as shown in FIG. 3. The surface 112 includes the laser "lens" 120, and the collection lens 130, 140. The other side 128 of the substrate includes a plurality of slits. In addition, both sides of the substrates include alignment marks. 112 include the alignment marks 312, 314, which are alignment marks for the electronic beams. The front side 128 includes the alignment marks 316, 318 which are the alignment for the front-to-back transfer.

The substrate may be fabricated as follows. A quartz substrate of size 2 mm×2 mm×0.5 mm is obtained. The quartz substrate can be fused silica, for example. The substrate is first evaporatively coated with a thin film of chromium using evaporation. The result in structure is then coated with polymethylmetachrylate or PMMA.

Slits 130 are opened in the front side 128. This can be formed as two different openings, e.g., a first window 320 which is 100 microns wide and 500 microns long. A plurality of slits 325 are formed to the side of that window. These can be 1–2 microns wide, and 500 microns long. The slits have 10 micron separations from one another, and may be separated by 5 microns from the window 320. The slits and optical window pattern can be opened in the PMMA using e-beam lithography. The chromium may be subsequently wet edged in the open areas to form better openings.

Thereafter, the surface is coated with a thick layer of photoresist in order to protect the surface. The back side 112 is also coated with photoresist. The front side alignment marks are used to form front side holes and open holes in the photoresist using an optical mask and UV exposure. The surface is then coated with metal for liftoff. The metal is removed using E-beam alignment marks. All of the photoresist can also be removed.

A PMMA layer is then deposited on the bottom of substrate 112. Two different diffractive optical elements are formed in the PMMA layer. The PMMA laser lens 120 is formed which is 200 microns wide 500 microns long. The PMMA collection lens 135 is formed that is 400 microns wide 500 microns long. These are formed using E-beam lithography and developed using acetone.

The sensing element is then formed and mounted in a housing 400. The housing 400 includes all of the structure therein, including the diode laser and optical receiver.

This system can produce significant advantages. In addition, modifications in this system are contemplated. For example, a diffractive optical element can be used in place of the optical window 320 in order to collect the scattered light more efficiently.

Figure 5:
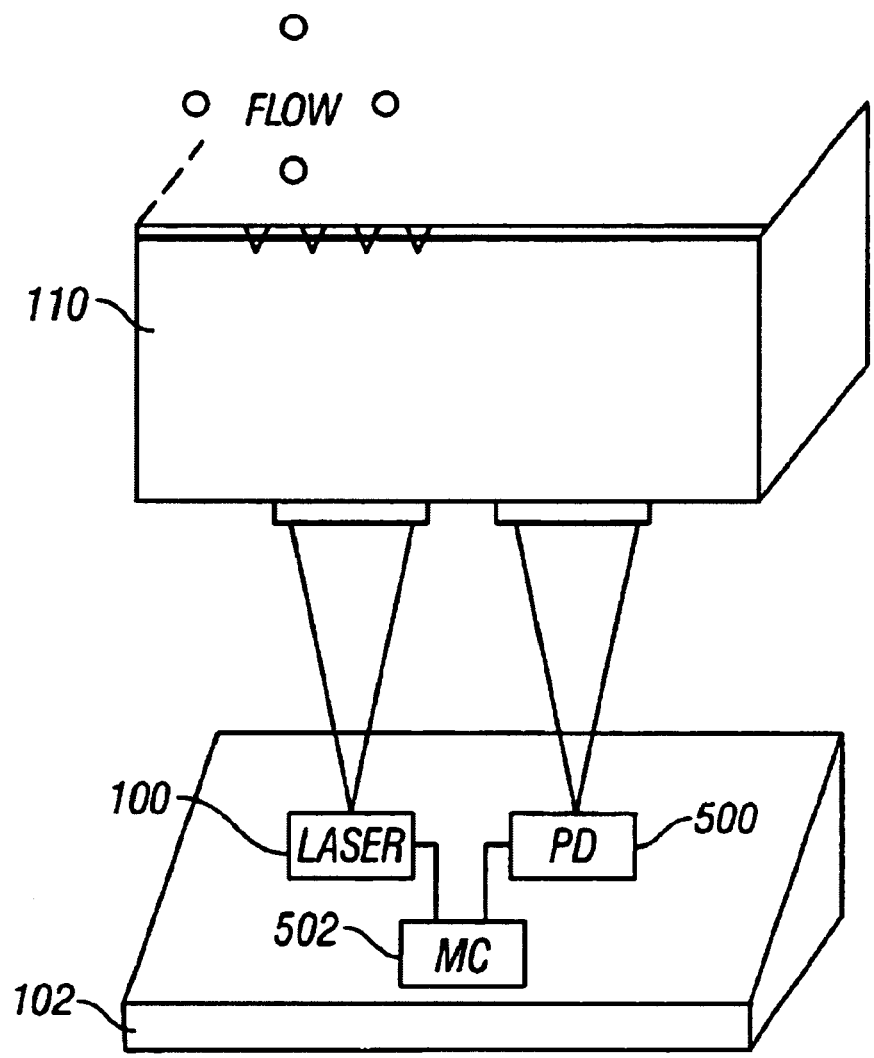
FIG. 5 shows another embodiment using a common substrate to support the laser and the optical detector.

In another embodiment, shown in FIG. 5, the detector is mounted directly on the substrate 102. This avoids the use of fibers, and reduces the parts count. In this embodiment, both the laser 100, and photodiode 500 are mounted on a single substrate 102. A controller 502 may also be mounted on the substrate. The controller may control both the laser 100 and the photodiode 500. For example, the controller can instruct the laser what and when to emit. It can receive information from the photodiode, and interpret it in view of timing information sent to the laser.

Figure 6A:
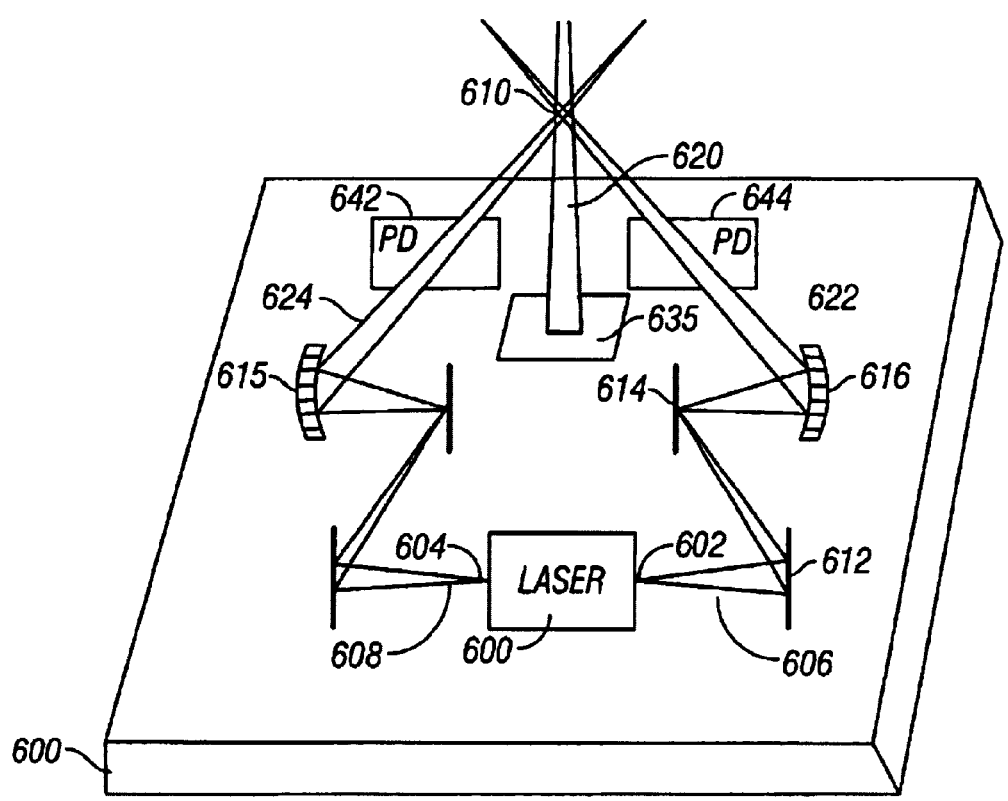
FIGS. 6A and 6B show two embodiments of integrated optical sensors.
Figure 6B:
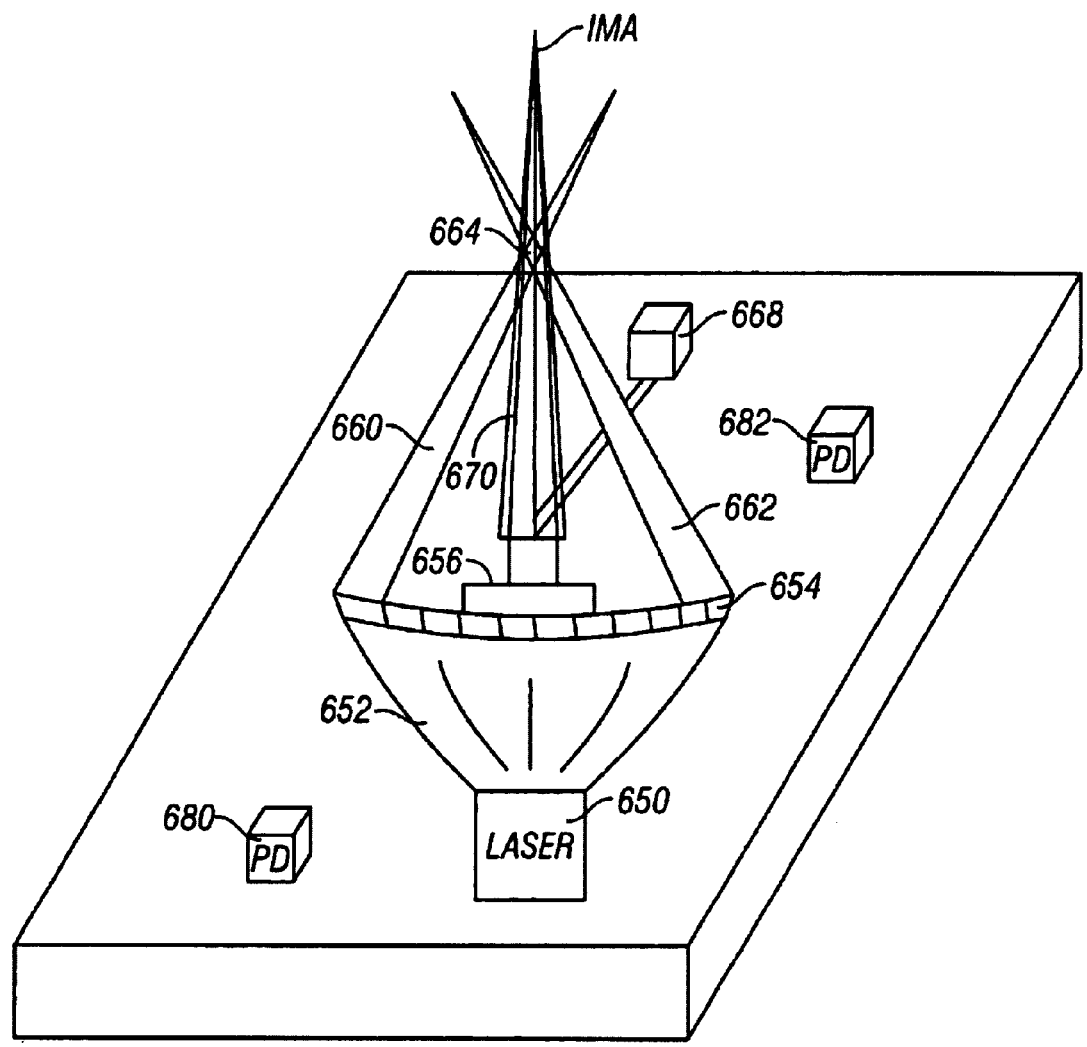

Another embodiment which forms a fiber optic particle probe is shown in FIGS. 6A and 6B. A diode laser is used along with curved gratings and detectors. FIG. 6A shows a configuration with a laser 600 emitting along both sides 602 and 604. The two-sided emission provides laser output arms 606, 608. Beam 606 is reflected by mirrors 612, 614, and coupled to a curved grating 616. Beam 608 is correspondingly coupled to grating 618. The outputs 622, 624 of gratings 616, 618 are recombined off the surface at a point 610. The point 610, for example, can be 3 millimeters over the surface of the substrate 600. A fringe pattern is formed by the recombination.

The fringe pattern is centered on a second laser beam, called the IMAX beam, that has been created by a second laser source 635. The IMAX beam provides information on the size of the particle and as such is a particle-sizing beam 620.

Light is scattered by the particles and received by photodetectors 642, 644, which are mounted on the substrates in locations to receive the scattered light from the particles at the point 610. The phase shift of the detectors is proportional to the particle size at the point 610. An on-chip or off processor or controller may receive the signals from the photodetectors and calculate the particle size.

FIG. 6B shows an alternative embodiment in which fringes in space are formed. A single ended diode 650 produces an output 652. The diode laser output 652 is allowed to diverge onto a curved grating 654, which is blocked in its center shown as 656.

The grating 654 redirects the light 652 into two separated light beams 660, 662, which are separated by the blocked portion 656. The two light beams 660 and 662 are directed to intersect 3 millimeters off the surface at the point 664. A separate laser 668 produces an IMAX beam 670. As in the FIG. 6A embodiment, photodetectors 680, 682 detect the scattered light and use the scattered light to find particle size.

Figure 7:
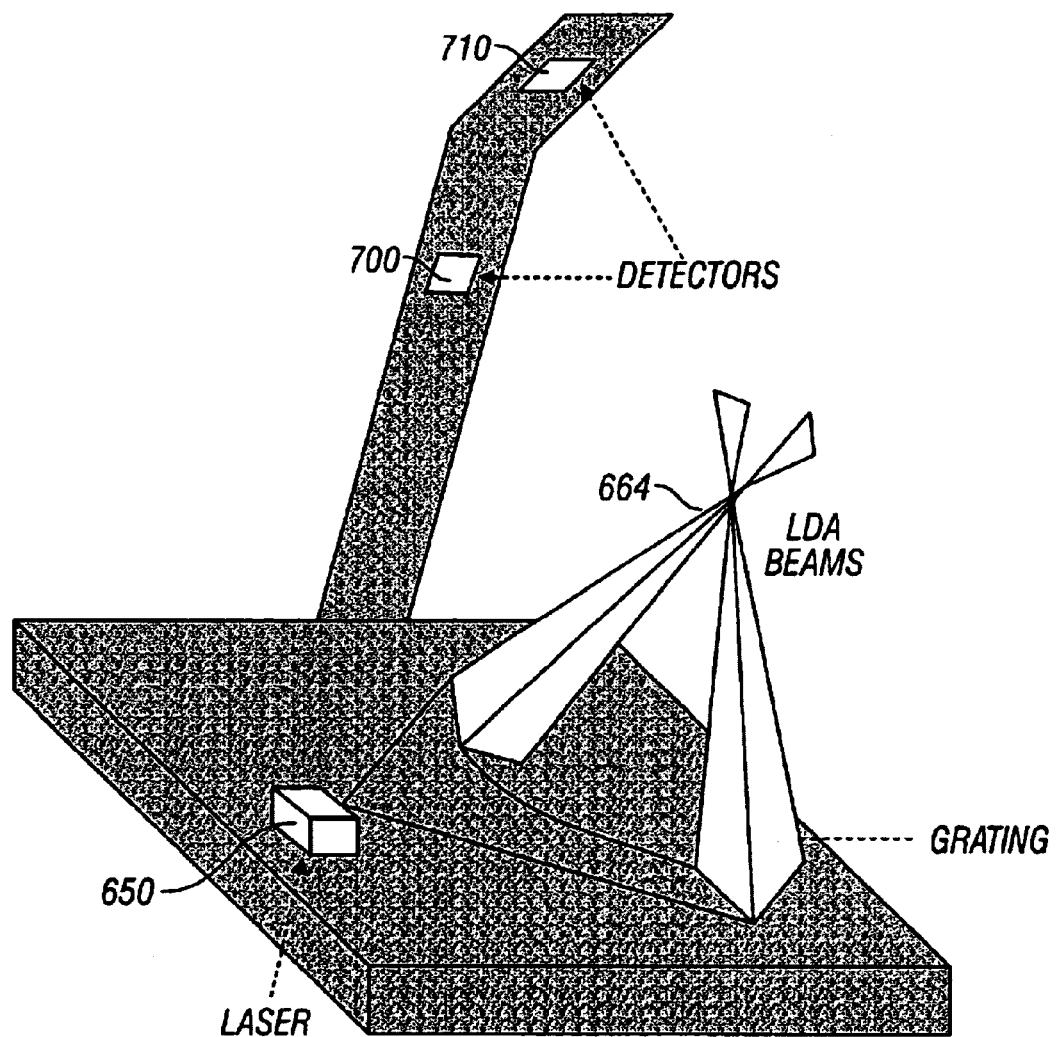
FIG. 7 shows an integrated optical sensor based on a phased Doppler technique.

Another embodiment shown in FIG. 7 uses a phased Doppler technique without the technique using the IMAX beam. The same structure of the laser 650 and curved grating 654 forming the LDA beams intersecting above the surface is defined. Detectors 700, 710 are located on an arm extending above the surface to receive the beam. This technique works best for particle sizes close to the laser wavelength.

As in the other embodiments, the scattered light gathered by the two detectors exhibits a phase shift that is proportional to the phase particle size.

Although only a few embodiments have been defined in detail above, other modifications are possible.

What is claimed is:

1. A sensor, comprising:
a laser element, producing a diverging beam; and
a single substrate, including a first diffractive optical element placed to receive the diverging beam and to produce a fringe beam based thereon, a mask with openings placed to receive the fringe beam from the first diffractive optical element and to interface with particles being detected which scatter said fringe beam, and a second diffractive element receiving scattered light.

2. A sensor as in claim 1, wherein said single substrate includes a first surface which includes both said first and second diffractive optical elements.

3. A sensor as in claim 2, further comprising a second surface, opposite said first surface, including a pattern formed thereon which receives particles crossing the pattern, and light crossing the particles being collected as said scattered light.

4. A sensor as in claim 1, further comprising a detector, receiving said scattered light, and producing a signal indicative of a property of particles being detected.

5. A sensor as in claim 4, further comprising a housing, wherein said laser element, said single substrate, and said detector are coupled within said housing.

6. A sensor as in claim 1, wherein said substrate is a substrate formed of a quartz.

7. A sensor as in claim 1, wherein a dimension of each side of said quartz substrate is less than 1000 microns.

8. A sensor as in claim 6, wherein said quartz substrate has a first surface with said first and second diffractive optical elements formed thereon and a second surface with diverging fringes which is placed in an area of light collection.

9. A method of measuring particles, comprising:
placing a first surface of a transparent substrate into contact with a source of particles;
illuminating said particles with a laser via a diffractive optical element on a second surface of said substrate to form interference fringes and receiving scattered light from said particles via a second diffractive element; and monitoring said received light to determine information about said particles.

10. A method as in claim 9, wherein said diffractive elements are formed by depositing PMMA on the surface of the substrate.

11. A method as in claim 9, wherein said substrate is formed of quartz.

12. A method as in claim 9, further comprising forming alignment marks on opposite sides of the substrate.

13. A method as in claim 12, wherein said alignment marks are formed as positive structures on one side, and lack of positive structures on the other side.

14. An integrated shear stress sensor, comprising:

a housing;

a laser diode coupled to said housing in a location to emit light;

a sensing element, formed by a transparent substrate, having a first surface adjacent said laser diode to receive illumination therefrom and a second surface adjacent a top portion of said housing to sense particle movement; and an optical sensor, also coupled to said housing, coupled adjacent to said substrate to receive collected light therefrom; and optical slits on the second side of the substrate forming a fringe pattern in an area of said second side of said substrate, said fringe pattern interfering with said particles.

15. A sensor as in claim 14, wherein said first surface of said substrate includes two diffractive optical elements, a first optical element receiving said laser beam from said laser diode, and a second of said optical elements receiving collected light.

16. A sensor as in claim 15, wherein said diffractive optical elements are formed from PMMA layers on the substrate.

17. A sensor as in claim 14, wherein said optical sensor includes an avalanche photodiode.

18. A method of sensing particles, comprising:

illuminating particles with laser light via a series of slits which form a fringe pattern; and detecting interference with said fringe pattern as detecting particle flow.

19. A method as in claim 18 wherein said detecting comprises extracting shear stress information from the interference.

20. A method as in claim 18, further comprising directing an additional laser beam to the particles to detect a size of the particles.

21. A method as in claim 18, wherein said illuminating comprises forming two beams, and recombining said two beams to form said fringe pattern.

22. A method as in claim 21, wherein said two beams are formed by a laser producing two output beams.

23. A method as in claim 21, wherein said two beams are formed by a single grating with a blocked part.

24. A method as in claim 18, wherein said detecting comprises detecting light in two locations, and determining a phase shift therebetween.

* * * * *